(12) United States Patent
Harling et al.

(10) Patent No.: US 6,492,388 B1
(45) Date of Patent: Dec. 10, 2002

(54) SUBSTITUTED ISOQUINOLINE DERIVATIVES AND THEIR USE AS INTICONVULSANTS

(75) Inventors: John David Harling; Mervyn Thompson, both of Harlow (GB)

(73) Assignee: SmithKline Beecham p.l.c., Brentford (GB)

( * ) Notice: Subject to any disclaimer, the term of this patent is extended or adjusted under 35 U.S.C. 154(b) by 0 days.

(21) Appl. No.: 10/019,104

(22) PCT Filed: Jun. 29, 2000

(86) PCT No.: PCT/GB00/02500

§ 371 (c)(1),
(2), (4) Date: Apr. 12, 2002

(87) PCT Pub. No.: WO01/02366

PCT Pub. Date: Jan. 11, 2001

(30) Foreign Application Priority Data

Jul. 2, 1999 (GB) ............................................. 9915589

(51) Int. Cl.$^7$ ..................... C07D 217/04; C07D 409/12; A61K 31/47
(52) U.S. Cl. ........................................ 514/310; 546/143
(58) Field of Search ........................... 514/310; 546/143

(56) References Cited

U.S. PATENT DOCUMENTS 4,022,900 A    5/1977   Mathison

FOREIGN PATENT DOCUMENTS

| WO | WO 97 48683 | 12/1997 |
| WO | WO 98 41507 | 9/1998 |
| WO | WO 98 41508 | 9/1998 |
| WO | WO99 21836 | 5/1999 |
| WO | WO99 31068 | 6/1999 |

Primary Examiner—Zinna Northington Davis
(74) Attorney, Agent, or Firm—Linda E. Hall; Stephen Venetianer; Charles M. Kinzig

(57) ABSTRACT

The invention relates to novel isoquinolines and their use as anticonvulsants and in the treatment of a variety of disorders.

14 Claims, No Drawings

SUBSTITUTED ISOQUINOLINE DERIVATIVES AND THEIR USE AS INTICONVULSANTS

This is a 371 of International Application PCT/GB00/02500, filed Jun. 29, 2000, which claims priority from GB 9915589.7 filed Jul. 2, 1999.

This invention relates to novel compounds, to processes for preparing them, and to their use as therapeutic agents.

Prior art document U.S. Pat. No. 4,022,900 (Marion Laboratories Inc.) discloses benzamido-1, 2, 3,4-tetrahydroisoquinolines having anti-hypertensive properties. Prior art documents International Application Publication Numbers WO 97/48683, WO98/41507, WO 98/41508, WO 97/48683, WO 99/21836 and WO 99/31068 (SmithKline Beecham) disclose isoquinolinyl benzamide derivatives and their use as anticonvulsants.

It has now been surprisingly found that carboxamide compounds of formula (I) below possess anti-convulsant activity and are therefore believed to be useful in the treatment and/or prevention of anxiety, mania, depression, panic disorders and/or aggression, disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy including post-traumatic epilepsy, Parkinson's disease, psychosis, migraine, cerebral ischaernia, Alzheimer's disease and other degenerative diseases such as Huntingdon's chorea, schizophrenia, obsessive compulsive disorders (OCD), neurological deficits associated with AIDS, sleep disorders (including circadian rhythm disorders, insomnia & narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, multiple sclerosis (MS) and motor neurone disease, ataxias, muscular rigidity (spasticity), temporomandibular joint dysfunction, and amyotrophic lateral sclerosis (ALS).

Accordingly, in a first aspect, the present invention provides a compound of formula (I) or pharmaceutically acceptable salt thereof:

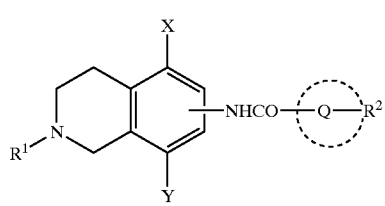

(I)

wherein:
Q is a monocyclic or bicyclic aryl or heteroaryl ring;
$R^1$ is hydrogen:
$R^2$ is hydrogen or up to three substituents selected from halogen, $NO_2$, CN, $N_3$, $CF_3O-$, $CF_3S-$, $CF_3SO_2-$, $CF_3CO-$, $C_{1-6}$alkyl, $C_{1-6}$alkenyl, $C_{1-6}$alkynyl, $C_{1-6}$perfluoroalkyl, $C_{3-6}$cycloalkyl, $C_{3-6}$cycloalkyl-$C_{1-4}$alkyl-, $C_{1-6}$alkylO—, $C_{1-6}$alkylCO—, $C_{3-6}$cycloalkylO—, $C_{3-6}$cycloalkylCO—, $C_{3-6}$cycloalkyl-$C_{1-4}$alkylO—, $C_{3-6}$cycloalkyl-$C_{1-4}$alkylCO—, phenyl, phenoxy, benzyloxy, benzoyl, phenyl-$C_{1-4}$alkyl-, $C_{1-6}$alkylS—, $C_{1-6}$alkylSO$_2$—, $(C_{1-4}$alkyl$)_2$NSO$_2$—, $(C_{1-4}$alkyl$)$NHSO$_2$—, $(C_{1-4}$alkyl$)_2$NCO—, $(C_{1-4}$alkyl$)$NHCO—, or CONH$_2$, or —NR$^3$R$^4$ where R$^3$ is hydrogen or $C_{1-4}$ alkyl, and R$^4$ is hydrogen, $C_{1-4}$alkyl, formyl, —CO$_2$C$_{1-4}$alkyl, or —COC$_{1-4}$alkyl, or two R$^2$ groups together form a carbocyclic ring that is saturated or unsaturated and unsubstituted or substituted by —OH or =O:

X is halogen, $C_{1-6}$ alkoxy, $C_{1-6}$ alkyl, or $C_{1-6}$ perfluoroalkyl, and;

Y is hydrogen, halogen, $C_{1-6}$ alkoxy, $C_{1-6}$ alkyl, or $C_{1-6}$ perfluoroalkyl;

with the proviso that the following compounds are excluded:
N-(5-Iodo-1,2,3,4-tetrahydroisoquinolin-7-yl)-4-azidobenzamide, and;
N-(5-iodo-1,2,3,4-tetrahydroisoquinolin-7-yl)-5-benzoyl-2-methoxybenzamide.

The compounds of this invention are typically (tetrahydroisoquinolin-7-yl) carboxamides.

The ring system Q is typically unsubstituted or substituted phenyl or unsubstituted or substituted thiophenyl. When two $R^2$ groups form a carbocyclic ring, this is typically a 5–7-membered ring, and Q may be a naphthalene, indane, or indanone ring system.

Alkyl groups of formula (I), including alkyl groups that are part of other moieties such as alkoxy or acyl, may be straight or branched chain. Phenyl groups in $R^2$, including phenyl groups that are part of other moieties, may be substituted independently with one or more groups selected from halogen, $C_{1-6}$ alkyl, $C_{1-6}$ alkoxy, or $C_{1-6}$ alkylcarbonyl. Suitable $C_{3-6}$ cycloalkyl groups include cyclopropyl, cyclobutyl, cyclopentyl, and cyclohexyl. Suitable halo substituents include fluoro, chloro, iodo and bromo.

A suitable group of compounds of this invention consists of compounds of formula (IA):

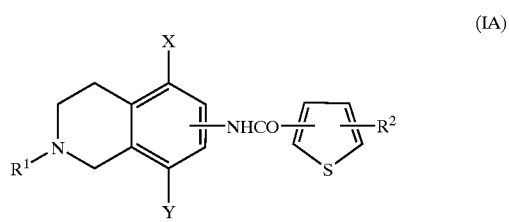

(IA)

another suitable group of compounds consists of compounds of formula (IB):

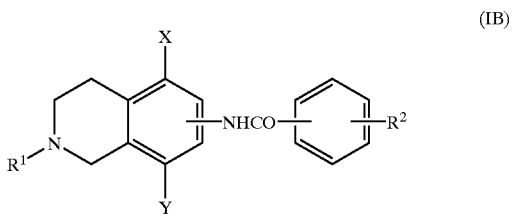

(IB)

wherein $R^1$, $R^2$, X, and Y are as hereinbefore defined.

A suitable group of compounds of formula (I) are those wherein;
$R^1$ is hydrogen;
$R^2$ is hydrogen or one or more of the following groups: methyl, ethyl, n-butyl, iso-propyl, t-butyl, phenyl, methoxy, ethoxy, iso-propoxy, n-butoxy, cyclopropylmethoxy, phenoxy, benzyloxy, amino, acetylamino, nitro, azido, cyano, bromo, chloro, fluoro, iodo, acetyl, pivaloyl, iso-butyroyl, benzoyl, iodobenzoyl, trifluoromethyl, perfluoroethyl, trifluoromethoxy, trifluoroacetyl, methanesulfonyl, n-propylsulfonyl, isopropylsulfonyl, dimethylsulfamoyl, or two $R^2$ groups form a benzene, cyclopentane or cyclopentanone ring;

X is chloro, bromo, iodo, fluoro $C_{1-6}$ perfluoroalkyl, and;

Y is hydrogen, halogen, $C_{1-6}$ alkoxy, $C_{1-6}$ alkyl, or, $C_{1-6}$ perfluoroalkyl.

A preferred group of compounds of formula (I) are those wherein;

$R^1$ is hydrogen;

$R^2$ is hydrogen or one or more of the following groups; methyl, ethyl, iso-propyl, n-butyl, t-butyl, phenyl, methoxy, ethoxy, iso-propoxy, phenoxy, acetoxy, nitro, cyano, bromo, chloro, fluoro, iodo, acetyl, pivaloyl, trifluoromethyl, pentafluoroethyl, azido, trifluoromethoxy;

X is iodo, chloro, bromo or trifluoromethyl, and;

Y is hydrogen, chloro, bromo, iodo or trifluoromethyl.

The following compounds are examples of compounds of formula (I), but do not limit the invention in any way:

N-(5-Chloro-1,2,3,4-tetrahydroisoquinolin-7-yl)-5-chlorothiophene-2-carboxamide
N-(5-Chloro-1,2,3,4-tetrahydroisoquinolin-7-yl)-3-chloro-4-ethoxy benzamide
N-(5-Chloro-1,2,3,4-tetrahydroisoquinolin-7-yl)-3-cyano-4-iso-propyl benzamide
N-(5-Chloro-1,2,3,4-tetrahydroisoquinolin-7-yl)-4-methoxy-3-trifluoromethyl benzamide
N-(5-Chloro-1,2,3,4-tetrahydroisoquinolin-7-yl)-3-cyano-4-methoxybenzamide
N-(5-Chloro-1,2,3,4-tetrahydroisoquinolin-7-yl)-3-chloro-4-methoxybenzamide
N-(5-Chloro-1,2,3,4-tetrahydroisoquinolin-7-yl)-3-bromo-4-ethoxybenzamide
N-(5-Chloro-1,2,3,4-tetrahydroisoquinolin-7-yl)-3-acetyl-4-iso-propoxybenzamide
N-(5-Chloro-1,2,3,4-tetrahydroisoquinolin-7-yl)-3-acetyl-4-ethylbenzamide
N-(5-Chloro-1,2,3,4-tetrahydroisoquinolin-7-yl)-3-bromo-4-ethylbenzamide
N-(5-Chloro-1,2,3,4-tetrahydroisoquinolin-7-yl)-3-chloro-4-iso-propoxybenzamide
N-(5-Chloro-1,2,3,4-tetrahydroisoquinolin-7-yl)-4-ethoxy-3-trifluoromethyl benzamide
N-(5-Chloro-1,2,3,4-tetrahydroisoquinolin-7-yl)-3-cyano-4-ethoxy benzamide
N-(5-Chloro-1,2,3,4-tetrahydroisoquinolin-7-yl)-3-acetyl-4-ethoxy benzamide
N-(5-Chloro-1,2,3,4-tetrahydroisoquinolin-7-yl)-4-ethyl-3-trifluoromethyl benzamide
N-(5,8-Dichloro-1,2,3,4-tetrahydroisoquinolin-7-yl )-4-methoxy-3-trifluoromethylbenzamide
N-(5-Chloro-1,2,3,4-tetrahydroisoquinolin-7-yl)-3-bromo-4-methoxybenzamide
N-(5-Chloro-1,2,3,4-tetrahydroisoquinolin-7-yl)-3-fluoro-4-methoxybenzamide
N-(5-Chloro-1,2,3,4-tetrahydroisoquinolin-7-yl)-3-bromo-4-iso-propoxybenzaniide
N-(5-Chloro-1,2,3,4-tetrahydroisoquinolin-7-yl)-4-methoxy-3-pentafluoroethyl benzamide
N-(5-Chloro-1,2,3,4-tetrahydroisoquinolin-7-yl )-4-iso-propoxy-3-trifluoromethyl benzamide
N-(5-Bromo-1,2,3,4-tetrahydroisoquinolin-7-yl)-3-bromo-4-methoxybenzamide
N-(5-Bromo-1,2,3,4-tetrahydroisoquinolin-7-yl)-4-methoxy-3-trifluoromethyl benzamide
N-(5-Bromo-1,2,3,4-tetrahydroisoquinolin-7-yl)-4-ethoxy-3-trifluoromethyl benzamide
N-(5-Bromo-1,2,3,4-tetrahydroisoquinolin-7-yl)-3-cyano-4-ethoxybenzamide
N-(5-Bromo-1,2,3,4-tetrahydroisoquinolin-7-yl)-3-acetyl-4-ethoxybenzamide
N-(5-Bromo-1,2,3,4-tetrahydroisoquinolin-7-yl)-3-acetyl-4-ethoxybenzamide
N-(5-Bromo-1,2,3,4-tetrahydroisoquinolin-7-yl)-3-chloro-4-ethoxybenzamide
N-(5-Bromo-1,2,3,4-tetrahydroisoquinolin-7-yl)-3-bromo-4-ethoxybenzamide
N-(5-Bromo-1,2,3,4-tetrahydroisoquinolin-7-yl)-3-cyano-4-iso-propylbenzamide
N-(5-Trifluoromethyl-1,2,3,4-tetrahydroisoquinolin-7-yl)-3-chloro-4-ethoxybenzamide
N-(5-Trifluoromethyl-1 ,2,3,4-tetrahydroisoquinolin-7-yl)-4-methoxy-3-trifluoromethylbenzamide
N-(5-Trifluoromethyl-1,2,3,4-tetrahydroisoquinolin-7-yl)-3-fluoro-4-methoxybenzamide
N-(5,8-Dichloro-1,2,3,4-tetrahydroisoquinolin-7-yl)-3-chloro-4-ethoxybenzamide
N-(5,8-Dichloro-1,2,3,4-tetrahydroisoquinolin-7-yl)-3-bromo-4-ethoxybenzamide
N-(5,8-Dichloro-1,2,3,4-tetrahydroisoquinolin-7-yl)-3-cyano-4-ethoxybenzamide
N-(5,8-Dichloro-1,2,3,4-tetrahydroisoquinolin-7-yl)-3-acetyl-4-ethoxybenzamide
N-(5,8-Dichloro-1,2,3,4-tetrahydroisoquinolin-7-yl)-3-fluoro-4-methoxybenzamide
N-(5,8-Dichloro-1,2,3,4-tetrahydroisoquinolin-7-yl)-3-bromo-4-methoxybenzamide
N-(5,8-Dichloro-1,2,3,4-tetrahydroisoquinolin-7-yl)-3-acetyl-4-iso-propoxybenzamide
N-(5-Chloro-1,2,3,4-tetrahydroisoquinolin-7-yl)-3-cyano-4-iso-propoxybenzamide.

When synthesised these compounds are often in salt form such as the hydrochloride or trifluoroacetate, and such salts also form part of this invention. Such salts may be used in preparing pharmaceutically acceptable salts. The compounds and their salts may be obtained as solvates such as hydrates, and these also form part of this invention.

The above compounds and pharmaceutically acceptable salts thereof, especially the hydrochloride, and pharmaceutically acceptable solvates, especially hydrates, form a preferred aspect of the present invention.

The administration of such compounds to a mammal may be by way of oral, parenteral, sub-lingual, nasal, rectal, topical or transdermal administration.

An amount effective to treat the disorders hereinbefore described depends on the usual factors such as the nature and severity of the disorders being treated and the weight of the mammal. However, a unit dose will normally contain 1 to 1000 mg, suitably 1 to 500 mg, for example an amount in the range of from 2 to 400 mg such as 2, 5, 10, 20, 30, 40, 50, 100, 200, 300 and 400 mg of the active compound. Unit doses will normally be administered once or more than once per day, for example 1, 2, 3, 4, 5 or 6 times a day, more usually 1 to 4 times a day, such that the total daily dose is normally in the range, for a 70 kg adult of 1 to 1000 mg, for example 1 to 500 mg, that is in the range of approximately 0.01 to 15 mg/kg/day, more usually 0.1 to 6 mg/kg/day, for example 1 to 6 mg/kg/day.

It is greatly preferred that the compound of formula (I) is administered in the form of a unit dose composition, such as an oral unit dose including sub-lingual, rectal, topical or parenteral (especially intravenous) composition.

Such compositions are prepared by admixture and are suitably adapted for oral or parenteral administration, and as such may be in the form of tablets, capsules, oral liquid preparations, powders, granules, lozenges, reconstitutable powders, injectable and infusable solutions or suspensions or suppositories. Orally administrable compositions are preferred, in particular shaped oral compositions, since they are more convenient for general use.

Tablets and capsules for oral administration are usually presented in a unit dose, and contain conventional excipients such as binding agents, fillers, diluents, tabletting agents, lubricants, disintegrants, colorants, flavourings, and wetting agents. The tablets may be coated according to well known methods in the art. Suitable fillers for use include cellulose, mannitol, lactose and other similar agents. Suitable disintegrants include starch, polyvinylpyrrolidone and starch derivatives such as sodium starch glycollate. Suitable lubricants include, for example, magnesium stearate. Suitable pharmaceutically acceptable wetting agents include sodium lauryl sulphate.

These solid oral compositions may be prepared by conventional methods of blending, filling, tabletting or the like. Repeated blending operations may be used to distribute the active agent throughout those compositions employing large quantities of fillers. Such operations are, of course, conventional in the art.

Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents. Oral formulations also include conventional sustained release formulations, such as tablets or granules having an enteric coating.

For parenteral administration, fluid unit dose forms are prepared containing the compound and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure to ethylene oxide before suspending in the sterile vehicle. Advantageously, a surfactant or wetting agent is included in the composition to facilitate uniform distribution of the compound of the invention.

As is common practice, the compositions will usually be accompanied by written or printed directions for use in the medical treatment concerned.

Accordingly, the present invention further provides a pharmaceutical composition for use in the treatment and/or prophylaxis of anxiety, mania, depression, panic disorders and/or aggression, disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy including post-traumatic epilepsy, Parkinson's disease, psychosis, migraine, cerebral ischaemia, Alzheimer's disease and other degenerative diseases such as Huntingdon's chorea, schizophrenia, obsessive compulsive disorders (OCD), neurological deficits associated with AIDS, sleep disorders (including circadian rhythm disorders, insomnia & narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, multiple sclerosis (MS) and motor neurone disease, ataxias, muscular rigidity (spasticity), temporomandibular joint dysfunction, and amyotrophic lateral sclerosis (ALS) which comprises a compound of formula (I), or a pharmaceutically acceptable salt or solvate thereof, and a pharmaceutically acceptable carrier.

The present invention also provides a method of treatment and/or prophylaxis of anxiety, mania, depression, panic disorders and/or aggression, disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy including post-traumatic epilepsy, Parkinson's disease, psychosis, migraine, cerebral ischaernia, Alzheimer's disease and other degenerative diseases such as Huntingdon's chorea, schizophrenia, obsessive compulsive disorders (OCD), neurological deficits associated with AIDS, sleep disorders (including circadian rhythm disorders, insomnia & narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, multiple sclerosis (MS) and motor neurone disease, ataxias, muscular rigidity (spasticity), temporomandibular joint dysfunction, and amyotrophic lateral sclerosis (ALS) comprising administering to the sufferer in need thereof an effective or prophylactic amount of a compound of formula (I), or a pharmaceutically acceptable salt or solvate thereof.

In a further aspect the invention provides the use of a compound of formula (I), or a pharmaceutically acceptable salt or solvate thereof, for the manufacture of a medicament for the treatment and/or prophylaxis of anxiety, mania, depression, panic disorders and/or aggression, disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy including post-traumatic epilepsy, Parkinson's disease, psychosis. migraine, cerebral ischaemia, Alzheimer's disease and other degenerative diseases such as Huntingdon's chorea, schizophrenia, obsessive compulsive disorders (OCD), neurological deficits associated with AIDS, sleep disorders (including circadian rhythm disorders, insomnia & narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, multiple sclerosis (MS) and motor neurone disease, ataxias, muscular rigidity (spasticity), temporomandibular joint dysfunction, and amyotrophic lateral sclerosis (ALS).

In a further aspect the invention provides the use of a compound of formula (I), or a pharmaceutically acceptable salt or solvate, thereof as a therapeutic agent, in particular for the treatment and/or prophylaxis of anxiety, mania, depression, panic disorders and/or aggression, disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy including post-traumatic epilepsy, Parkinson's disease, psychosis, migraine, cerebral ischaemia, Alzheimer's disease and other degenerative diseases such as Huntingdon's chorea, schizophrenia, obsessive compulsive disorders (OCD), neurological deficits associated with AIDS, sleep disorders (including circadian rhythm disorders, insomnia & narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, multiple sclerosis (MS) and motor neurone disease, ataxias, muscular rigidity (spasticity), temporomandibular joint dysfunction, and amyotrophic lateral sclerosis (ALS).

In a further aspect, the present invention provides a process for the preparation of compounds of formula (I) as hereinbefore defined which process comprises reacting a compound of formula (II);

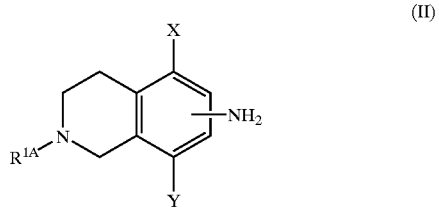

(II)

wherein $R^{1A}$ is $R^1$ or preferably a group convertible to $R^1$, and $R^1$, X, and Y are as hereinbefore defined, with a compound of formula (III)

(III)

wherein
Q is as hereinbefore defined;
Y is a leaving group such as Cl or OH, and;
$R^{2A}$ represents hydrogen or up to three substituents as hereinbefore defined for $R^2$ wherein the $R^{2A}$ groups may independently be $R^2$ groups or groups convertible to $R^2$;
and where required converting an $R^{1A}$ or $R^{2A}$ group to a $R^1$ or $R^2$ group respectively;
converting one $R^1$ or $R^2$ group to another $R^1$ or $R^2$ group;
converting a salt product to the free base or a pharmaceutically acceptable salt, or converting a free base product to a pharmaceutically acceptable salt.

Reaction of a compound of formula (III) which is an acid chloride (Y=Cl) will lead directly to the hydrochloride salt. Suitable solvents include ethyl acetate or dichloromethane, optionally in the presence of a base such as triethylamine. When the compound of formula (III) is an aromatic acid (Y=OH), conventional conditions for condensation of such acids with amines may be used, for example reacting the components in a mixture of (dimethylaminopropyl)-ethyl-carbodiimide/hydroxybenzotriazole in a suitable solvent such as dimethyl formamide.

Conversions of an $R^{1A}$ or $R^{2A}$ group to a $R^1$ or $R^2$ group typically arise when a protecting group is needed during the above coupling reaction or during the preparation of the reactants by the procedures described below. Interconversion of one $R^1$ or $R^2$ group to another typically arises when one compound of formula (I) is used as the immediate precursor of another compound of formula (I) or when it is easier to introduce a more complex or reactive substituent at the end of a synthetic sequence.

The compound of formula (II), wherein $R^{1A}$ is hydrogen or trifluoroacetyl and X and Y are both chloro may be prepared from the compound of formula (II) wherein $R^{1A}$ is hydrogen or trifluoroacetyl, X is chloro, and Y is hydrogen by reaction with N-chloromorpholine in glacial acetic acid.

The compound of formula (II) wherein $R^{1A}$ is hydrogen or trifluoroacetyl, X is chloro, and Y is hydrogen may be prepared from the compound of formula (IV) wherein $R^{1A}$ is hydrogen or trifluoroacetyl, X is chloro and Y is hydrogen by reduction with tin (II) chloride in concentrated hydrochloric acid.

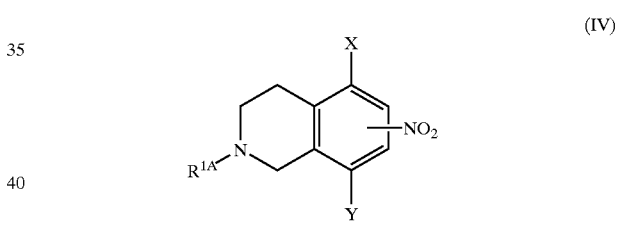

(IV)

The compound of formula (IV) wherein $R^{1A}$ is hydrogen or trifluoroacetyl, X is chloro and Y is hydrogen may be prepared from the compound of formula (IV) wherein X is iodo and Y is hydrogen by heating in the presence of copper (I) chloride in an inert atmosphere.

The compound of formula (IV) wherein $R^{1A}$ is hydrogen or trifluoroacetyl, X is iodo and Y is hydrogen may be prepared from the compound of formula (V) wherein $R^{1A}$ is hydrogen or trifluoroacetyl and Y is hydrogen by reaction with N-iodosuccinimide in triflic acid according to the procedure of G. A. Olah et al., J.Org. Chem., 1993, 58, 3194.

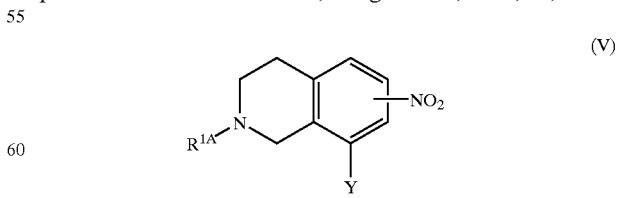

(V)

The compound of formula (V) wherein $R^{1A}$ is hydrogen and Y is hydrogen may be prepared from the compound of formula (VI) wherein Y is hydrogen by hydrolysis with potassium carbonate in methanol.

(VI)

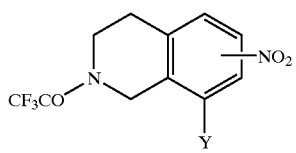

The compound of formula (VI) wherein Y is hydrogen may be prepared by reaction of N-(nitrophenyl)ethyl trifluoroacetamide and paraformaldehyde in acidic conditions using the procedure of Stokker, Tet.Lett.,1996, 37, 5453. N-(nitrophenyl)ethyl trifluoroacetamides can be prepared from readily available materials by reaction of trifluoracetic anhydride with lutidine and nitrophenethylamine hydrochloride, as illustrated in the Descriptions below.

Compounds of formula (II) may also be prepared from the corresponding aminoisoquinoline (or its nitro-analogue) of formula (VII)

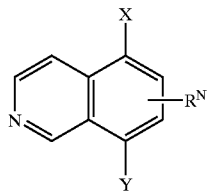

where $R^N$ is $NH_2$ or $NO_2$ and X and Y are as hereinbefore defined by reaction with a compound $R^{1A}Z$ where Z is a leaving group such as halogen, especially Iodo, or tosylate and $R^{1A}$ is benzyl or 4-methoxybenzyl to obtain an intermediate of formula (VIII).

(VIII)

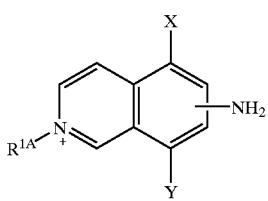

which can be reduced, for example using sodium borohydride, or hydrogenated, for example using hydrogen and a palladium/activated carbon catalyst, to obtain a tetrahydroisoquinoline of formula (II). When the compound of formula (VIII) is replaced by a nitroisoquinoline, the nitro group is converted to an amino group in the hydrogenation step.

When the intended $R^1$ is hydrogen, the nitrogen atom of the tetrahydroisoquinoline or isoquinoline molecule is preferably protected conventionally, prior to the coupling step that forms the carboxamide of formula (I), for example by tert.-butoxycarbonyl, trifluoroacetyl or benzyl. The compound can be deprotected under standard conditions, for example using trifluoroacetic acid/methylene chloride or potassium carbonate in aqueous methanol, catalytic hydrogenolysis.

Amino/nitro-isoquinolines of formula (VIII) and the reagents used are commercially available, or can be prepared from commercially available materials using conventional procedures described in the literature.

The substituents X and Y may be introduced during any of the procedures above, for example by conventional substitution of the aromatic ring of compounds of formula (IV), (V) or (VIII) or may be present on commercially available starting materials usable in the above described procedures. Most suitably the substituents X and Y are introduced to a compound of formula (IX)

(IX)

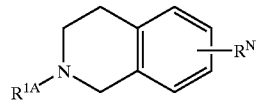

where $R^N$ and $R^{1A}$ are as hereinbefore defined. For example X as halogen may be incorporated by reaction with a halosuccinimide, or $X=CF_3$ may be introduced by displacement of iodo with copper(I)trifluoroacetate as illustrated in the descriptions below.

Compounds of formula (III) may be prepared by further substitution of commercially available benzoic acid or thiophene carboxylic acid derivatives using conventional procedures, or by oxidation of corresponding substituted benzyl alcohols. Alternatively benzoic acids can be prepared from correspondingly substituted phenols, for example by formation of the acetate, conversion to an acetophenone and then to the desired acid. Examples of these procedures are documented in WO 98/41507 and WO98/41508.

Where the above described intermediates are novel compounds, they also form part of this invention.

The preparation of compounds of this invention is further illustrated by the following Descriptions and Examples, which do not limit the invention in any way:

Description 1

N-2-(4-Nitrophenyl)ethyl-trifluoroacetamide

A solution of trifluoroacetic anhydride (10.6 ml) in dichloromethane (100 ml) was added dropwise to a stirred solution of 2,6-lutidine (17.44 ml) and 4-nitrophenethylamine hydrochloride (15.2 g; 75 mmol) at 0° C. The mixture was stirred at 25° C. overnight under argon and then washed with dilute citric acid (×2), brine and dried over $Na_2SO_4$. The material in the organic phase gave the title compound D1 as a pale yellow solid (19.04 g).

Description 2

7-Nitro-1,2,3,4-tetrahydro-2-trifluoracetyl-isoquinoline

The product from Description 1 (2.26 g; 9.15 mmol) and paraformaldehyde (0.45 g; 14.4 mmol) in acetic acid (10 ml) and conc. $H_2SO_4$ (15 ml) were stirred at 25° C. for 20 h according to the procedure of G. E. Stokker., Tet. Lett., 1996, 37, 5453. Work up afforded the title compound D2 as a white solid (2.17 g).

$^1H$ NMR (CDCl$_3$) δ: 3.10 (2H, m), 3.92 (2H, m), 4.85+ 4.92 (2H, 2xs), 7.38 (1H, t), 8.10 (2H, m); m/z (EI): 274 (M$^+$)

Description 3

7-Nitro-1,2,3,4-tetrahydroisoquinoline

The product from Description 2 (17.22 g; 63 mmol) was hydrolysed at room temperature using a solution of potassium carbonate (46.6 g) in 10% aqueous methanol (660 ml). Work-up with dichloromethane gave the title compound (11 g).

Description 4

5-Iodo-7-nitro-1,2,3,4-tetrahydroisoquinoline

The product from Description 3 (750 mg; 3.9 mmol) and N-iodosuccinimide (1.13 g) in triflic acid (5 ml) was stirred at 25° C. overnight according to the procedure of G. A. Olah et al., J.Org. Chem., 1993, 58, 3194. The mixture was poured cautiously into saturated NaHCO$_3$ and then extracted into ether (2×). The combined organic extracts were washed with aqueous sodium thiosulfate, dried (MgSO$_4$) and evaporation in vacuo gave a residue. Chromatography on Kieselgel 60 in 2% methanol-dichloromethane gave the title compound (650 mg).

Description 5

7-Amino-5-iodo-1,2,3,4-tetrahydroisoquinoline

A solution of the product from Description 4 (650 mg, 2.14 mmol) in ethanol (20 ml) at 50° C. was treated with a solution of tin (II) chloride (1.42 g) in c. HCl (3 ml). The resultant yellow solution was basified with 10% aqueous sodium hydroxide and the product extracted into dichloromethane. Flash chromatography on Kieselgel 60 (5% methanol-dichloromethane) gave the title compound (428 mg; 73%).

Description 6

5-Iodo-7-nitro-2-trifluoroacetyl-1,2,3,4-tetrahydroisoquinoline

The title compound was prepared from the product from Description 2 using a procedure similar to that of Description 4.

m/z (API$^+$): 401 (MH$^+$; 45%).

Description 7

5-Chloro-7-nitro-2-trifluoroacetyl-1,2,3,4-tetrahydroisoquinoline

The product from Description 6 (810 mg) in dry DMF (15 ml) was treated with copper (I) chloride (605 mg) and heated at 125° C. under argon for 18 h. After cooling, the mixture was concentrated in vacuo and the residue partitioned between ethyl acetate and water. The organic layer was then washed with water (×3), aqueous sodium thiosulfate, brine and dried (MgSO$_4$). Evaporation in vacuo gave the title compound as a red gum (519 mg).

$^1$H NMR (CDCl$_3$) δ: 3.09 (2H, m), 3.96 (2H, m), 4.85, 4.92 (2H, 2s, rotamers), 7.99 (1H, m), 8.20 (1H, m).

Description 8

7-Amino-5-chloro-2-trifluoroacetyl-1,2,3,4-tetrahydroisoquinoline

A solution of the product from Description 7 (2.14 mmol) in ethanol (20 ml) at 50° C. was treated with a solution of tin (II) chloride (1.42 g) in c. HCl (3 ml). The resultant yellow solution was basified with 10% aqueous sodium hydroxide and the product extracted into dichloromethane. Flash chromatography on Kieselgel 60 (5% methanol-dichloromethane) gave the title compound.

$^1$H NMR (CDCl$_3$) δ: 2.84 (2H, m), 3.67 (2H, brs), 3.83 (2H, m), 4.61, 4.67 (2H, 2s, rotamers), 6.33 (1H, m), 6.65 (1H, m).

Description 9

7-Amino-5,8-dichloro-2-trifluoroacetyl-1,2,3,4-tetrahydroisoquinoline

Chlorination of the product from Description 8 (150 mg; 0.54 mmol) with N-chloromorpholine (100 mg; 0.89 mmol) in glacial acetic acid (6 ml) for 30 min at 25° C. followed by basic work-up similar to that of Description 8 gave the title compound (70 mg).

m/z (API$^+$): 315, 313 (MH$^+$; 50% expected isotope pattern)

Description 10

7-Amino-5-bromo-2-trifluoroacetyl-1,2,3,4-tetrahydroisoquinoline

The title compound was prepared from the product from Description 6 and copper (II) bromide using a method similar to that of Description 7 followed by tin (II) chloride reduction according to the procedure used in Description 8.

$^1$H NMR (CDCl$_3$) δ: 2.86 (2H, m), 3.68 (2H, brs), 3.85 (2H, m), 4.62, 4.69 (2H, 2s, rotamers), 6.39 (1H, m), 6.85 (1H, m).

Description 11

7-Amino-5-trifluoromethyl-2-trifluoroacetyl-1,2,3,4-tetrahydroisoquinoline

The title compound was prepared from the product from Description 6 and potassium trifluoroacetate using a method similar to that of Preparation 6 followed by hydrogenation over 10% palladium on carbon (100 mg) in ethanol at atmospheric pressure overnight. The catalyst was removed by filtration through a pad of Kieselguhr and evaporation in vacuo gave the title compound.

$^1$H NMR (CDCl$_3$) δ: 2.98 (2H, brm), 3.82 (4H, m), 4.67, 4.72 (2H, 2s, rotamers), 6.60 (1H, m), 6.88 (1H, m).

Preparation 1

4-tert-Butyl-phenoxyacetate

A mixture of 3-tert-butylphenol (25.25 g, 0.1680 mole), acetic anhydride (34.31 g, 0.336 mole) and sodium acetate (13.78 g, 0.1680 mole) was heated at 100° C. for 2 h. On cooling the mixture was poured into water (200 ml) and extracted with ethyl acetate (200 ml). The combined organic extracts were dried over sodium sulfate and concentrated in vacuo to afford the acetate compound as an oil (33.33 g).

Preparation 2

4-tert-Butyl-2-hydroxy Acetophenone

A mixture of the acetate of Preparation 1 (33.23 g, 0.173 mole) and AlCl$_3$ (25.61 g. 0.192 mole) was placed in an oil bath preheated to 120° C. and stirred mechanically. Then the oil bath temperature was raised to 165° C. and maintained for 45 min before being allowed to cool to 120° C. Then water was added dropwise into the reaction mixture (4×250 ml) to steam distil the product (bath temp 190–200° C.). The distillate was extracted with ether and the combined organic extracts were dried over sodium sulfate and concentrated in vacuo to afford 4-tert-butyl-2-hydroxy acetophenone as an oil (18.05 g).

Preparation 3

4-tert-Butyl-2-methoxy Acetophenone

A suspension of 4-tert-butyl-2-hydroxy acetophenone (12.65 g), potassium carbonate (13.14 g) and dimethyl sulfate (8.99 ml) in acetone (200 ml) was refluxed for 48 h. After cooling, the mixture was filtered. The solvent was then removed in vacuo and the residue taken up in dichloromethane and washed with brine. The organic layer was dried over sodium sulfate and concentrated in vacuo to afford a yellow oil (12.05 g).

Preparation 4

4-tert-Butyl-2-methoxybenzoic Acid

The acetophenone of Preparation 3 (11.0 g, 53 mmol) was added to a solution of sodium hydroxide (28.68 g), sodium hypochlorite (182 ml, 12% w/w) and water (70 ml) at 80° C. with stirring. After heating for 1.25 h, the mixture was cooled to 0° C. and a solution of sodium metabisulphite (41.1 g) in water (170 ml) was added. The mixture was stirred for 15 min and then acidified (pH1) with conc. HCl (45 ml). Work-up with ethyl acetate gave the title compound as a white solid (8.9 g).

$^1$H NMR (DMSO-d$^6$) δ: 1.30 (9H, s), 3.85 (3H, s), 6.96–7.12 (2H, m), 7.60 (1H, d), 12.30–12.60 (1H, br).

Preparation 5

5-Bromo-2,4-dimethoxybenzoic Acid

To a solution of 2,4-dimethoxybenzoic acid (4.0 g, 0.022 mol) in chloroform (60 ml) was added bromine (1.13 ml, 0.022 mol) in chloroform (20 ml) dropwise. After stirring overnight at room temperature the precipitate was filtered off and dried to afford the title compound as a white solid (2.87 g).

Preparation 6

2,4-Dimethoxy-5-trifluoromethylbenzoic Acid

5-Bromo-2,4-dimethoxybenzoic acid methyl ester (1.5 g; 5.4 mmol) in DMF (25 ml) and toluene (8 ml) under argon was treated with potassium trifluoroacetate (1.53 g; 10.1 mmol) and copper (I) iodide (2.1 g, 10.9 mmol). The mixture was heated to 170° C. with removal of water (Dean/Stark), and then at 155° C. overnight; then allowed to cool, poured into ether and water and filtered through Kieselguhr. The organic layer was dried (Na$_2$SO$_4$) and concentrated in vacuo to give a brown solid. Chromatography on Kieselgel 60 with 1:1 ether/petrol gave a white solid (1.03 g) which was hydrolysed in 1:1 methanolic:aqueous NaOH (50 ml) at 50° C. Work-up gave the title compound as a white solid (1 g).

Preparation 7

3-Bromo-4-ethoxybenzoic Acid

The title compound was prepared from 4-ethoxybenzoic acid in a manner similar to that of Preparation 5.

$^1$H NMR (DMSO-D$_6$) δ: 1:45 (3H, t, J=7 Hz), 4.26 (2H, q, J=7 Hz), 7.26 (1H, d, J=9 Hz), 7.98 (1H, dd, J=2, 9 Hz), 8.12 (1H, d, J=2 Hz)

Preparation 8

4-Methoxy-3-trifluoromethylbenzoic Acid

The title compound was prepared from 3-bromo4-methoxybenzoic acid and potassium trifluoroacetate in a manner similar to that of Preparation 6.

$^1$H NMR (DMSO-D$_6$) δ: 3.78 (3H, s), 7.18 (1H, d, J=9 Hz), 7.90 (1H, d, J=2 Hz), 8.00 (1H, dd, J=2, 9 Hz), 12.70–13.10 (1H, br,exchangeable)

Preparation 9

4-Methoxy-3-trifluoromethylbenzoyl Chloride

The title compound was prepared from 4-methoxy-3-trifluoromethylbenzoic acid with oxalyl chloride and DMF in chloroform at room temperature [D. Levin, Chem. Br., 1977, 20] followed by evaporation in vacuo.

Preparation 10

3-Bromo-4-ethylbenzoic Acid

The title compound was prepared from 4-ethylbenzoic acid.

$^1$H NMR (DMSO-D$_6$) δ: 1.20 (3H, t,J=7 Hz), 2.78 (2H, q, J=7 Hz), 7.50 (1H, d, J=8 Hz), 7.90 (1H, dd, J=2, 8 Hz), 8.07 (1H, d, J=8 Hz

Preparation 11

4-iso-Propyl-3-trifluoromethylbenzoic Acid

Prepared as described in Preparation 6 from methyl 3-bromo4-iso-propylbenzoate and isolated as a white solid.

m/z (API): 231.1 [M—H].

Preparation 12

3-Cyano4-iso-propylbenzoic acid

The title compound was prepared from 4-isopropylbenzoic acid similar to that described in Procedure 1.

$^1$H NMR (DMSO-D$_6$) δ: 1.07 (6H, d, J=7 Hz), 3.13 (1H,m, overlapped), 7.48 (1H, d, J=7 Hz), 7.96 (1H, dd, J=2, 8 Hz)), 8.00 (1H, d, J=2 Hz).

Preparation 13

Methyl 3-bromo-4-iso-propoxybenzoate

Methyl 3-bromo-4-hydroxybenzoate (2.5 g, 10.8 mmol) in DMF (35 ml) was treated with potassium carbonate (3.0 g, 21.6 mmol), 2-iodopropane (2.76, 21.6 mmol) and then stirred at 25° C. for 48 h. Work-up with ethyl acetate gave the title compound (3.0 g).

$^1$H NMR (250 MHz, CDCl$_3$) δ: 1.41 (6H, d, J=7 Hz), 3.89 (3H, s), 4.66 (1H, m), 6.90 (1H, d, J=8 Hz), 7.93 (1H, dd, J=8, 2 Hz), 8.22 (1H, d, J=2 Hz)

Preparation 14

Methyl 3-cyano-4-iso-propoxybenzoate

Methyl 3-bromo-4-iso-propoxybenzoate (2.0 g, 7.3 mmol) and copper(I)cyanide in N-methyl pyrrolidone (50 ml) were heated under vigorous reflux for 4 h. Work-up with ethyl acetate gave the title compound (1.0 g).

$^1$H NMR (250 MHz, CDCl$_3$) δ: 1.56 (6H, d, J=7 Hz), 4.05 (3H, s), 4.88 (1H, m), 7.13 (1H, d, J=8 Hz), 8.31 (1H, dd, J=8, 2 Hz), 838 (1H, d, J=2 Hz)

Preparation 15

3-Cyano-4-iso-propoxybenzoic Acid

Saponification of P14 gave the acid as an off white solid.

$^1$H NMR (250 MHz, CDCl$_3$) δ: 1.35 (6H, d, J=7 Hz), 4.67 (1H, m), 6.90 (1H, d, J=8 Hz), 8.11 (1H, dd, J=8, 2 Hz), 8.19 (1H, d, J=2 Hz)

Preparation 16 iso-Propyl 3-acetyl-4-iso-propoxybenzoate

The bromo ester (2.5 g, 8.3 mmol) in dry dioxan (30 ml) was treated with (1-ethoxyvinyl)-tributyl tin (3.58 g, 9.9 mmol) followed by tetrakis triphenylphosphine palladium (o) (0.48 g, 0.4 mmol) and heated at 100° for 18 h. After cooling, the mixture was acidified and aqueous work-up and extraction into ethyl acetate gave a coloured oil (5.6 g). Flash chromatography on Kieselgel 60 [hexane to 20% EtAc/hexane gave the title compound as a yellow oil (2.3 g).

m/z (API$^+$): 265.2 (MH$^+$, 90%).

Preparation 17

3-Acetyl-4-iso-propoxybenzoic Acid

Saponification of the ester P16 (2.3 g) gave the title compound as a white solid (1.3 g).

$^1$H NMR (250 MHz, CDCl$_3$) δ: 1.48 (6H, d, J=7 Hz), 2.63 (3H, s), 4.80 (1H, m), 7.00 (1H, d, J=8 Hz), 8.17 (1H, dd, J=8, 2 Hz), 8.46 (1H, d, J=2 Hz)

Preparation 18

Methyl 3-cyano-4-ethoxybenzoate $^1$H NMR (250 MHz, CDCl$_3$) δ: 1.53 (3H, d, J=7 Hz), 3.91 (3H, s), 4.25 (2H, q, J=7 Hz), 7.02 (1H, d, J=8 Hz), 8.25 (1H, dd, J=8,2Hz), 8.32 (1H, d, J=2 Hz).

Preparation 19

3-Acetyl-4-ethoxybenzoic Acid

Prepared in a similar manner to that described for Preparations 16 and 17.

$^1$H NMR (250 MHz, CDCl$_3$) δ: 1.53 (3H, t, J=7 Hz), 2.65 (3H, s), 4.23 (2H, q, J=7 Hz), 7.01 (1H, d, J=8 Hz), 8.19 (1H, dd, J=8, 2 Hz), 8.48 (1H, d, J=2 Hz).

Preparation 20

3-Chloro-4-ethoxybenzoic Acid $^1$H NMR (DMSO-D$_6$) δ: 1.39 (3H, t, J=7 Hz), 4.20 (2H, q, J=7 Hz), 7.22 (1H, d, J=7 Hz), 7.87 (2H, m).

Procedure 1a

Methyl 2-methoxy-5-cyano-4-iso-propylbenzoate

Copper (I) cyanide (550 mg, 6 mmol) was added to a solution of methyl 2-methoxy-5-bromo-4-iso-propylbenzoate (861 mg) in N-methyl-2-pyrrolidinone (30 ml). The mixture was stirred under argon and boiled under reflux for 4 h. The mixture was cooled, poured into excess ice/water and ethyl acetate and filtered. The organic phase was separated, washed with water, brine and dried(MgSO$_4$). Evaporation gave a crude brown solid which was purified by chromatography on silica gel eluting with ethyl acetate/n-hexane (1:4). The product was obtained as a white solid (523 mg).

$^1$H NMR (250 MHz, CDCl$_3$) δ: 1.33 (6H, d, J=7 Hz), 3.38 (1H, sep, J=7Hz), 3.89 (3H, s), 3.98 (3H, s), 6.91 (1H, s), 8.08 (1H, s); m/z (API$^+$): 234 (MH$^+$, 30%).

Procedure 1b

2-Methoxy-5-cyano-4-iso-propylbenzoic Acid

2N NaOH (1.25 ml) was added to a solution of the methyl ester P1a (490 mg) in methanol (10 ml). The solution was stirred overnight at room temperature. The solution was then diluted with water, concentrated in vacuo and washed with ethyl acetate. The aqueous phase was then acidified with 2N HCl and extracted with ethyl acetate. The extract was washed with brine, dried (MgSO$_4$) and evaporated to dryness giving the product as a white solid (418 mg).

$^1$H NMR (250 MHz, CDCl$_3$) δ: 1.35 (6H, d, J=7 Hz), 3.43 (1H, sep, J=7 Hz), 4.14 (3H,s), 7.00 (1H, s), 8.41 (1H, s); m/z (API$^+$): 220 (MH$^+$, 100%).

Procedure 2

N-(5-Chloro-2-trifluoroacetyl-1,2,3,4-tetrahydroisoquinolin-7-yl)-5-chlorothiophene-2-carboxamide 5-Chloro-2-thenoic acid (90 mg, 0.55 mmol) and oxalyl chloride (0.05 ml, 0.6 mmol) in dichloromethane (2 ml) was treated with 2 drops of DMF and stirred at at 25° C. for 30 min. Evaporation in vacuo gave a solid which was added to a solution of D8 (155 mg, 0.55 mmol) in dichloromethane (10 ml) containing triethylamine (0.1 ml). After 20 h at room temperature, the mixture was diluted with ethyl acetate (100 ml) and washed with 1N HCl (100 ml), water (100 ml), brine (50 ml) and dried (MgSO$_4$). Evaporation in vacuo gave the title compound as a white solid (148 mg).

$^1$H NMR (CDCl$_3$) δ: 2.96 (2H, m), 3.88 (2H, m), 4.73, 4.77 (2H, 2s, rotamers), 6.95 (1H, d, J=5 Hz), 7.20–7.60 (3H, m), 7.70 (1H, br); m/z (API$^+$) 424.8, 422.9 (MH$^+$; 100%).

EXAMPLE 1

N-(5-Chloro-1,2,3,4-tetrahydroisoquinolin-7-yl)-5-chlorothiophene-2-carboxamide

A suspension of the compound of Procedure 2 (148 mg, 0.35 mmol) and potassium carbonate (800 mg, 5.8 mmol) in 20% aqueous methanol (50 ml) was stirred at 25° C. for 18 h. Work-up similar to Description 3 gave the title compound as a white solid (68 mg).

$^1$H NMR (d$^6$DMSO) δ: 2.57 (2H, t), 2.97 (2H, t), 3.81 (2H, s), 7.28 (1H, d, J=5 Hz), 7.35 (1H, d, J=2 Hz), 7.68 (1H, d, J=2Hz), 7.89 (1H, d, J=5 Hz), 10.31 (1H, s); m/z (API$^+$): 329.1, 327.1 (MH$^+$; 30%)).

The following Examples were prepared using the methods previously described in the Descriptions, Preparations, Procedures, and Example 1.

EXAMPLE 2

N-(5-Chloro-1,2,3,4-tetrahydroisoquinolin-7-yl)-3-chloro-4-ethoxy Benzamide $^1$H NMR (270 MHz, CDCl$_3$) δ: 1.51 (3H, t, J =7 Hz), 2.73 (2H, t, J=7 Hz), 3.16 (2H, t, J=7 Hz), 3.97 (2H, s), 4.17 (2H, q, J=7Hz), 6.95 (1H, d, J=8 Hz), 7.50 (1H, d, J=1 Hz), 7.74 (1H, dd, J=8, 1 Hz), 7.82 (1H, s), 7.87 (1H, d, J=1 Hz); m/z (API$^+$): 365 (MH$^+$)

EXAMPLE 3

N-(5-Chloro-1,2,3,4-tetrahydroisoquinolin-7-yl)-3-cyano-4-iso-propyl Benzamide $^1$H NMR (270 MHz, CDCl$_3$) δ: 1.31 (6H, d, J=7 Hz), 2.74 (2H, t, J=7 Hz), 3.16 (2H, t, J=7 Hz), 3.44 (1H, m), 3.88 (2H, s), 7.29 (1H, d, J=1 Hz), 7.51 (2H, m), 7.87 (1H, s), 8.04 (1H, dd, J=7, 1 Hz), 8.10 (1H, d, J=1 Hz); m/z (API$^+$): 328 (MH$^+$).

EXAMPLE 4

N-(5-Chloro-1,2,3,4-tetrahydroisoquinolin-7-yl)-4-methoxy-3-trifluoromethyl Benzamide $^1$H NMR (250 MHz, CDCl$_3$) δ: 2.71–2.76 (2H, m), 3.14–3.19 (2H, m), 3.98 (ca 5H, s), 7.09 (1H, d, J=9 Hz), 7.29 (ca 1H, brs), 7.50 (1H, d, J=2 Hz), 7.80 (1H, br), 8.05–8.07 (2H, m); m/z (API$^+$): 385 (MH$^+$)

EXAMPLE 5

N-(5-Chloro-1,2,3,4-tetrahydroisoquinolin-7-yl)-3-cyano-4-methoxybenzamide $^1$H NMR (250 MHz, CDCl$_3$-d$_4$ MeOH): δ: inter atia 2.76–2.81 (2H, m), 3.13–3.18 (2H, m), 3.97 (2H, s), 4.03 (3H, s), 7.14 (1H, d, J=8 Hz), 7.34 (1H, s), 7.43 (1H, m), 7.64 (1H, s), 8.19–8.23 (2H, m); m/z (API$^+$): 342 (MH$^+$)

EXAMPLE 6

N-(5-Chloro-1,2,3,4-tetrahydroisoquinolin-7-yl)-3-chloro-4-methoxybenzamide $^1$H NMR (250 MHz, d$_4$ MeOH) δ: inter alia 2.69–2.74 (2H, m), 3.03–3.08 (2H, m), 3.88 (2H, s), 3.91 (3H, s), 7.14

(1H, d, J=8.5 Hz), 7.28 (1H, d, J=2 Hz), 7.63 (1H, d, J=2Hz), 7.84 (1H, dd, J=8, 2 Hz), 7.93 (1H, d, J=2 Hz); m/z (API$^+$) 351,353 (MH$^+$)

EXAMPLE 7

N-(5-Chloro-1,2,3,4-tetrahydroisoquinolin-7-yl)-3-bromo-4-ethoxybenzamide $^1$H NMR (250 MHz, d$_4$ MeOH) δ: 1.34 (3H, t, J=7 Hz), 2.61–2.66 (2H, m), 2.96–3.00 (2H, m), 3.80 (2H, s), 4.06 (2H, q, J=7 Hz), 6.98 (1H, d, J=7.5 Hz), 7.21 (1H, brs), 7.55 (1H, d, J=2 Hz), 7.78 (1H, dd, J=8,2Hz), 8.01 (1H, d, J=2Hz); m/z (API$^+$) 409, 411 (MH$^+$)

EXAMPLE 8

N-(5-Chloro-1,2,3,4-tetrahydroisoquinolin-7-yl)-3-acetyl-4-iso-propoxybenzamide $^1$H NMR (250 MHz, d$_4$ MeOH) δ: 1.16 (6H, d, J =6 Hz), 2.35 (3H, s), 2.46–2.51 (2H, m), 2.81–2.86 (2H, m), 3.66 (2H, S), 6.96 (1H, d, J=8.5 Hz), 7.06 (1H, d, J=2 Hz), 7.41 (1H, d, J=2 Hz), 7.79 (1H, dd, J=8.5, 2 Hz), 7.95 (1H, d, J=2 Hz); m/z (API$^+$): 387 (MH$^+$)

EXAMPLE 9

N-(5-Chloro-1,2,3,4-tetrahydroisoquinolin-7-yl)-3-acetyl-4-ethylbenzamide $^1$H NMR (250 MHz, d$_4$MeOH) δ: 1.03 (3H, t, J =7 Hz), 2.45 (3H, s), 2.57 (2H, m), 2.92 (2H, m), 3.75 (2H, s), 7.17 (1H, d, J=2Hz), 7.25 (1H, d, J=8.5 Hz). 7.51 (1H, d, J=2 Hz), 7.82 (1H, dd, J=8.5, 2 Hz), 8.07 (1H, d, J=2 Hz); m/z (API$^+$): 357 (MH$^+$)

EXAMPLE 10

N-(5-Chloro-1,2,3,4-tetrahydroisoquinolin-7-yl)-3-bromo-4-ethylbenzamide $^1$H NMR (CDCl$_3$) δ: 1.26 (3H, t), 2.77 (4H, m), 3.17 (2H, t), 3.98 (2H, s), 7.28 (1H, d), 7.34 (1H, d), 7.52 (1H, d), 7.72 (1H, dd), 7.81 (1H, s), 8.01 (1H, d); m/z (API+): 393.1 (M$^+$; 95%)

EXAMPLE 11

N-(5-Chloro-1,2,3,4-tetrahydroisoquinolin-7-yl)-3-chloro-4-iso-propoxybenzamide $^1$H NMR (CDCl$_3$) δ: 1.42 (6H, d), 2.74 (2H, t), 3.17 (2H, t), 3.99 (2H, s),4.67 (1H, m), 6.99 (1H, d), 7.28 (1H, d), 7.50 (1H, d), 7.69 (1H, s), 7.74 (1H, dd), 7.87 (1H, d); m/z (API+): 379.2 (MH$^+$;100%)

EXAMPLE 12

N-(5-Chloro-1,2,3,4-tetrahydroisoquinolin-7-yl)-4-ethoxy-3-trifluoromethyl Benzamide $^1$H NMR (CDCl$_3$) δ: 1.49 (3H, t), 2.74 (2H, t) 3.17 (2H, t), 4.00 (2H, s), 4.21 (2H, q), 7.07 (1H, d), 7.29 (1H, d), 7.51 (1H, d), 7.69 (1H, s), 8.03 (2H, m); m/z (API+): 399.1 (MH$^+$; 100%).

EXAMPLE 13

N-(5-Chloro-1,2,3,4-tetrahydroisoquinolin-7-yl)-3-cyano-4-ethoxy Benzamide $^1$H NMR (CDCl$_3$) δ: 1.53 (3H, t) 2.75 (2H, t) 3.17 (2H, t), 4.00 (2H, s), 4.24 (2H, q), 7.06 (1H, d), 7.27 (1H, d), 7.50 (1H, d), 7.66 (1H, s), 8.07 (2H, m); m/z (API+): 356.2 (MH$^+$;100%).

EXAMPLE 14

N-(5-Chloro-1,2,3,4-tetrahydroisoquinolin-7-yl)-3-acetyl-4-ethoxy Benzamide $^1$H NMR (CDCl$_3$) δ: 1.54 (3H, t), 2.68 (3H, s), 2.74 (2H, t), 3.17 (2H, t), 4.00(2H, s), 4.24(2H, q), 7.07 (1H, d), 7.29 (1H, d), 7.56 (1H, d), 7.91 (1H, s), 8.14 (1H, dd), 8.18 (1H, d); m/z (API+): 373.3 (MH$^+$;100%).

EXAMPLE 15

N-(5-Chloro-1,2,3,4-tetrahydroisoquinolin-7-yl)-4-ethyl-3-trifluoromethyl Benzamide $^1$H NMR (CDCl$_3$) δ: 1.29 (3H t), 2.75 (2H, t), 2.90 (2H, q), 3.18 (2H, t), 4.00 (2H, s), 7.31 (1H, d), 7.49 (1H, d), 7.53 (1H, d), 7.78 (1H, s), 7.97 (1H, dd), 8.08 (1H, d); m/z (API+): 383.2 (MH$^+$; 100%).

EXAMPLE 16

N-(5,8-Dichloro-1,2,3,4-tetrahydroisoquinolin-7-yl)-4-methoxy-3-trifluoromethylbenzamide $^1$H NMR (d$^6$DMSO) δ: 2.46 (2H, t), 2.78 (2H, t), 3.66 (2H, s), 3.82 (3H, s), 7.27 (1H, d, J=8 Hz), 7.38 (1H, s), 8.08 (1H, d, J=1 Hz), 8.10 (1H, dd, J=8, 1 Hz), 10.07 (1H, s); m/z (API$^+$): 420.9, 419.0, (MH$^+$, 100% expected isotope pattern).

EXAMPLE 17

N-(5-Chloro-1,2,3,4-tetrahydroisoquinolin-7-yl)-3-bromo-4-methoxybenzamide $^1$H NMR (CD$_3$OD) δ: 2.68 (2H, m), 3.01 (2H, m), 3.84 (2H, s), 3.86 (3H, s), 7.06 (1H, d, J=8 Hz), 7.29 (1H, d, J=1 Hz), 7.59 (1H, d, J=1 Hz), 7.84 (1H, dd, J=8, 2 Hz), 8.05 (1H, d, J=2 Hz); m/z (API+): 396.9 (MH$^+$;90%)., 395.0 (MH$^+$;60%).

EXAMPLE 18

N-(5-Chloro-1,2,3,4-tetrahydroisoquinolin-7-yl)-3-fluoro-4-methoxybenzamide $^1$H NMR (CD$_3$OD) δ: 2.67 (2H, t, J=7 Hz), 3.01 (2H, t, J=7 Hz), 3.81 (2H, s), 3.85 (3H, s), 7.11 (1H, t, J=10 Hz), 7.23 (1H, d, J=1 Hz), 7.58–7.63 (2H, m), 7.67 (1H, dd, J=8, 2 Hz); m/z (API+): 335 (MH$^+$;100%).

EXAMPLE 19

N-(5-Chloro-1,2,3,4-tetrahydroisoquinolin-7-yl)-3-bromo-4-iso-propoxybenzamide $^1$H NMR (CDCl$_3$) δ: 1.42 (6H, d, J=7 Hz), 2.73 (2H, t, J=7 Hz), 3.16 (2H, t, J=7 Hz), 3.97 (2H, s), 4.66 (2H, m), 6.94 (1H, d, J=8 Hz), 7.28 (1H, d, J=2 Hz), 7.49(1H, d, J=2 Hz), 7.74 (1H, s), 7.80 (1H, dd, J=8, 2 Hz), 8.03 (1H, d, J=2 Hz); m/z (API+): 424.9, 423.0 (MH$^+$; 100%).

EXAMPLE 20

N-(5-Chloro-1,2,3,4-tetrahydroisoquinolin-7-yl)-4-methoxy-3-pentafluoroethyl Benzamide $^1$H NMR (400 MHz, CDCl$_3$) δ: 2.73 (2H, t), 3.16 (2H, t), 3.95 (3H, s), 3.98 (2H, s), 7.1 (1H, d), 7.29 (1H, d), 7.50 (1H, d), 7.81 (1H, s), 8.01 (1H, d), 8.07 (1H, d) m/z (API$^+$): 435 (M+H)$^+$

EXAMPLE 21

N-(5-Chloro-1,2,3,4-tetrahydroisoquinolin-7-yl)-4-iso-propoxy-3-trifluoromethyl Benzamide $^1$H NMR (400 MHz, CDCl$_3$) δ: 1.40 (6H, d, J=6 Hz), 2.71 (2H, t), 3.14 (2H, t), 4.10 (2H, s), 4.72 (1H, m), 7.04 (1H, d), 7.47 (1H, d), 8.02 (3H, m); m/z (API$^+$): 413 (MH$^+$: 90%).

EXAMPLE 22

N-(5-Bromo-1,2,3,4-tetrahydroisoquinolin-7-yl)-3-bromo-4-methoxybenzamide $^1$H NMR (250 MHz, d$_6$ DMSO) δ: 2.56 (2H, t), 2.98 (2H, t), 3.83 (2H, s), 3.94 (3H, s), 7.26 (1H, d), 7.49 (1H, s), 7.93 (1H, s), 8.01 (1H, d), 8.23 (1H, d), 10.19 (1H, s); m/z (API$^+$): 440.8 (MH$^+$100%).

EXAMPLE 23

N-(5-Bromo-1,2,3,4-tetrahydroisoquinolin-7-yl)-4-methoxy-3-trifluoromethyl Benzamide $^1$H NMR (250 MHz, CDCl$_3$) δ: 2.73 (2H, t), 3.19 (2H, t), 3.99 (ca 5H, s), 7.08 (1H, d, J=9 Hz), 7.35 (1H, d), 7.70 (1H, d, J=2 Hz), 7.90 (1H, s), 8.07 (2H, m); m/z (API$^+$): 428.2 (MH$^+$)

EXAMPLE 24

N-(5-Bromo-1,2,3,4-tetrahydroisoquinolin-7yl)-4-ethoxy-3-trifluoromethyl Benzamide $^1$H NMR (CDCl$_3$) δ: 1.49 (3H, t), 2.73 (2H, t), 3.19 (2H, t), 3.98 (2H, s), 4.20 (2H, q), 7.05 (1H, d), 7.33 (1H, d), 7.70 (1H, d), 7.91 (1H, s), 8.03 (2H, m); m/z (API+): 443 (MH$^+$; 100%).

EXAMPLE 25

N-(5-Bromo-1,2,3,4-tetrahydroisoquinolin-7-yl)-3-cyano-4-ethoxybenzamide $^1$H NMR (250 MHz, d$_6$ DMSO) δ: 1.46 (3H, t), 2.63 (2H, t), 3.06 (2H, t), 3.91 (2H, s), 4.36 (2H, q), 7.45 (1H, d), 7.54 (1H, d), 7.97 (1H, d), 8.29 (1H, dd), 8.41 (1H, d), 10.29 (1H, s); m/z (API+): 400 (MH$^+$; 100%).

EXAMPLE 26

N-(5-Bromo-1,2,3,4-tetrahydroisoquinolin-7-yl)-3-acetyl-4-ethoxybenzamide $^1$H NMR (CDCl$_3$) δ: 1.54 (3H, t), 2.67 (3H, s), 2.70 (2H, t), 3.16 (2H, t), 3.98 (2H, s), 4.23 (2H, q), 7.07 (1H, d), 7.35 (1H, d), 7.72 (1H, d), 8.02 (1H, s), 8.13 (1H, dd), 8.19 (1H, d); m/z (API+): 417 (MH$^+$;100%).

EXAMPLE 27

N-(5-Bromo-1,2,3,4-tetrahydroisoquinolin-7-yl)-3-acetyl-4-iso-propoxybenzamide $^1$H NMR (250 MHz, CDCl$_3$) δ: 1.46 (6H, d, J=6 Hz), 2.66 (3H, s), 2.71 (2H, t), 3.16 (2H, t), 3.99 (2H, s), 4.81 (1H, m), 7.07 (1H, d, J=8.5 Hz), 7.35 (1H, d, J=2 Hz); (1H, d, J=2 Hz), 7.90(1H, s), 8.12(1H, dd, J=8.5, 2 Hz), 8.16(1H, d, J=2 Hz); m/z (API$^+$): 431 (MH$^+$)

EXAMPLE 28

N-(5-Bromo-1,2,3,4-tetrahydroisoquinolin-7-yl)-3-chloro-4-ethoxybenzamide $^1$H NMR (270 MHz, CDCl$_3$) δ: 1.51 (3H, t, J=7 Hz), 2.71 (2H, t, J=7 Hz), 3.16 (2H, t, J=7 Hz), 3.98 (2H, s), 4.18 (2H, q, J=7Hz), 6.98 (1H, d, J=8 Hz), 7.35 (1H, d, J=1 Hz), 7.66 (1H, d), 7.70(1H, s), 7.74(1H, dd, J=8, 1 Hz). 7.87 (1H, d, J=1 Hz); m/z (API$^+$): 409 (MH$^+$)

EXAMPLE 29

N-(5-Bromo-1,2,3,4-tetrahydroisoquinolin-7-yl)-3-bromo-4-ethoxybenzamide $^1$H NMR (270 MHz, CDCl$_3$) δ: 1.52 (3H, t, J=7 Hz), 2.71 (2H, t, J=7 Hz), 3.17 (2H, t, J=7 Hz), 3.98 (2H, s), 4.18 (2H, q, J=7 Hz), 6.94 (1H, d, J=8 Hz), 7.35 (1H, d, J=1 Hz), 7.66 (1H, d), 7.71 (1H, s), 7.79 (1H, dd, J=8, 1 Hz), 8.04 (1H, d, J=1 Hz); m/z (API$^+$): 454.9 (MH$^+$ 100%)

EXAMPLE 30

N-(5-Bromo-1,2,3,4-tetrahydroisoquinolin-7-yl)-3-cyano-4-iso-propylbenzamide $^1$H NMR (270 MHz, CDCl$_3$) δ: 1.35 (6H, d, J=7 Hz), 2.73 (2H, t, J=7 Hz), 3.18 (2H, t, J=7 Hz), 3.44 (1H, m), 3.99 (2H, s), 7.35 (1H, d, J=1 Hz), 7.53 (1H, d), 7.70 (1H, d), 7.95 (1H, s), 8.05 (1H, dd, J=7, 1 Hz), 8.11 (1H, d, J=1 Hz); m/z (API$^+$): 398 (MH$^+$).

EXAMPLE 31

N-(5-Trifluoromethyl-1,2,3,4-tetrahydroisoquinolin-7-yl)-3-chloro-4-ethoxybenzamide $^1$H NMR (270 MHz, CDCl$_3$) δ: 1.52 (3H,t, J=7 Hz), 2.91 (2H, m), 3.14 (2H, m) 7.66 (1H, (2H, s), 4.17 (2H, q, J=7 Hz), 6.98 (1H, d, J=8 Hz), 7.59 (1H, d, J=1 Hz), 7.66 (1H, d), 7.79 (2H, m), 7.88 (1H, d, J=1 Hz); m/z (API$^+$): 399 (MH$^+$ 90%)

EXAMPLE 32

N-(5-Trifluoromethyl-1,2,3,4-tetrahydroisoquinolin-7-yl)-4-methoxy-3-trifluoromethylbenzamide $^1$H NMR (270 MHz, CDCl$_3$) δ: 2.88 (2H, m), 3.10 (2H, m), 3.98 (3H, s), 4.05 (2H, m), 7.07 (1H, m), 7.61 (2H, m), 8.01 (1H, m), 8.08 (2H, m); m/z (API$^+$): 419 (MH$^+$ 85%)

EXAMPLE 33

N-(5-Trifluoromethyl-1,2,3,4-tetrahydroisoquinolin-7-yl)-3-fluoro-4-methoxy-benzamide $^1$H NMR (270 MHz, CDCl$_3$) δ: 2.91 (2H, m), 3.15 (2H, m), 3.97 (3H, s), 4.08 (2H, s), 7.03 (1H, t, J=7 Hz), 7.61 (4H, m), 7.78 (1H, brs); m/z (API$^+$): 369 (MH+ 85%)

EXAMPLE 34

N-(5,8-Dichloro-1,2,3,4-tetrahydroisoquinolin-7-yl)-3-chloro-4-ethoxybenzamide $^1$H NMR (CDCl$_3$) δ: 1.52 (3H, t), 2.76 (2H, t), 3.14 (2H, t), 4.00 (2H, s), 4.20 (2H, q), 7.00 (1H, d), 7.78 (1H, dd), 7.93 (1H, d), 8.29 (1H, s), 8.51 (1H, s); m/z (API$^+$); 399.0 (M$^+$; 100%)

EXAMPLE 35

N-(5,8-Dichloro-1,2,3,4-tetrahydroisoquinolin-7-yl)-3-bromo-4-ethoxybenzamide $^1$H NMR (CDCl$_3$) δ: 1.53 (3H, t), 2.78 (2H, t), 3.16 (2H, t), 4.05 (2H, s), 4.19 (2H, q), 6.97 (1H, d), 7.83 (1H, dd), 8.11 (1H, d), 8.28 (1H, s), 8.52 (1H, s); m/z (API$^+$): 445.0 (MH$^+$; 100%)

EXAMPLE 36

N-(5,8-Dichloro-1,2,3,4-tetrahydroisoquinolin-7-yl)-3-cyano-4-ethoxybenzamide $^1$H NMR (CDCl$_3$) δ: 1.54 (3H, t), 2.77 (2H, t), 3.15 (2H, t), 4.05 (2H, s), 4.26 (2H, q), 7.09 (1H, d), 8.10 (2H, m), 8.27 (1H, s), 8.49 (1H, s); m/z (API$^+$): 390.1 (M+; 100%)

EXAMPLE 37

N-(5,8-Dichloro-1,2,3,4-tetrahydroisoquinolin-7-yl)-3-acetyl-4-ethoxybenzamide $^1$H NMR (CDCl$_3$) δ: 1.54 (3H, t), 2.68 (3H, s), 2.75 (2H, t), 3.14 (2H, t), 4.03 (2H, s), 4.25 (2H, q), 7.09 (1H, d), 8.12 (1H, dd), 8.25 (1H, d), 8.40 (1H, s), 8.48 (1H, s); m/z (API$^+$): 407.1 (M$^+$; 100%)

EXAMPLE 38

N-(5,8-Dichloro-1,2,3,4-tetrahydroisoquinolin-7-yl)-3-fluoro-4-methoxybenzamide $^1$H NMR (CDCl$_3$) δ: 2.75 (2H, t), 3.14 (2H, t), 3.97 (3H, s), 4.02 (2H, s), 7.06 (1H, t), 7.66 (2H, m), 8.33 (1H, s), 8.50 (1H, s); m/z (API$^+$): 369.0 (M$^+$; 70%), 410.3 (M+K$^+$; 100%)

EXAMPLE 39

N-(5,8-Dichloro-1,2,3,4-tetrahydroisoquinolin-7-yl)-3-bromo-4-methoxybenzamide $^1$H NMR (CDCl$_3$) δ: 2.76 (2H, t), 3.14 (2H, t), 3.99 (3H, s), 4.03 (2H, s), 7.00 (1H, d), 7.86 (1H, dd), 8.11 (1H, d), 8.29 (1H, s), 8.51 (1H, s); m/z (API$^+$): 452.9 (M+Na$^+$; 100%)

EXAMPLE 40

N-(5,8-Dichloro-1,2,3,4-tetrahydroisoquinolin-7-yl)-3-acetyl-4-iso-propoxybenzamide $^1$H NMR (CDCl$_3$) δ: 1.46 (6H, d, J =6 Hz), 2.67 (3H, s), 2.75 (2H, t), 3.14 (2H, t), 4.03 (2H, s), 4.82 (1H, m), 7.09 (1H, d), 8.11 (1H, dd), 8.23 (1H, d), 8.40 (1H, s), 8.48 (1H, s); m/z (API$^+$): 421.0 (M$^+$; 100%)

EXAMPLE 41

N-(5-Chloro-1,2,3,4-tetrahydroisoquinolin-7-yl)-3-cyano-4-iso-propoxybenzamide m/z (API$^+$): 370.0 (MH$^+$; 100%, expected isotope pattern for M$^+$ $C_{20}H_{20}ClN_3O_2$)

Pharmacological Data

1. Binding Assay Method

WO 92/22293 (SmithKline Beecham) discloses compounds having anticonvulsant activity, including inter alia the compound trans-(+)-6-acetyl-4S-(4-fluorobenzoylamino)-3,4-dihydro-2,2-dimethyl-2H-1-benzopyran-3R-ol (hereinafter referred to as Compound A). It has been found that the compounds of WO 92/22293 bind to a novel receptor obtainable from rat forebrain tissue, as described in WO 96/18650 (SmithKline Beecham). The affinity of test compounds to the novel receptor site is assessed as follows.

Method

Whole forebrain tissue is obtained from rats. The tissue is first homogenised in buffer (usually 50 mM Tris/HCl, pH 7.4). The homogenised tissue is washed by centrifugation and resuspension in the same buffer, then stored at −70° C. until used.

To carry out the radioligand binding assay, aliquots of tissue prepared as above (usually at a concentration of 1–2 mg protein/ml) are mixed with aliquots of [3H]-Compound A dissolved in buffer. The final concentration of [3H]-Compound A in the mixture is usually 20 nM. The mixture is incubated at room temperature for 1 hour. [3H]-Compound A bound to the tissue is then separated from unbound [3H]-Compound A by filtration through Whatman GF/B glass fibre filters. The filters are then washed rapidly with ice-cold buffer. The amount of radioactivity bound to the tissue trapped on the filters is measured by addition of liquid scintillation cocktail to the filters followed by counting in a liquid scintillation counter.

In order to determine the amount of "specific" binding of [3H]-Compound A, parallel assays are carried out as above in which [3H]-Compound A and tissue are incubated together in the presence of unlabelled Compound A (usually 3 μM). The amount of binding of [3H]-Compound A remaining in the presence of this unlabelled compound is defined as "non-specific" binding. This amount is subtracted from the total amount of [3H]-Compound A binding (i.e. that present in the absence of unlabelled compound) to obtain the amount of "specific" binding of [3H]-Compound A to the novel site.

The affinity of the binding of test compounds to the novel site can be estimated by incubating together [3H]-Compound A and tissue in the presence of a range of concentrations of the compound to be tested. The decrease in the level of specific [3H]-Compound A binding as a result of competition by increasing concentrations of the compound under test is plotted graphically, and non-linear regression analysis of the resultant curve is used to provide an estimate of compound affinity in terms of pKi value.

Results

Compounds of this invention were active (pKi>6) in this test. For example, compounds of Examples 1, 10–12, 15, 38 gave pKi values greater than 7 and those of Examples 2–9, 13, 14, 16, 22–37, 39–41 gave values greater than 8.

2. MEST Test

The maximal electroshock seizure (MEST) threshold test in rodents is particularly sensitive for detecting potential anticonvulsant properties[1]. In this model, anticonvulsant agents elevate the threshold to electrically-induced seizures whilst proconvulsants lower the seizure threshold.

Method for Mouse Model

Mice (naive male, Charles River, U.K. CD-1 strain, 25–30 g) are randomdly assigned to groups of 10–20 and dosed orally or intraperitoneally at a dose volume of 10 ml/kg with various doses of compound (0.3–300 mg/kg) or vehicle. Mice are then subjected at 30 or 60 min post dose to a single electroshock (0.1 sec, 50 Hz, sine wave form) administered via corneal electrodes. The mean current and standard error required to induce a tonic seizure in 50% (CC$_{50}$) of the mice in a particular treatment group is determined by the 'up and down' method of Dixon and Mood (1948)[2]. Statistical comparisons between vehicle- and drug-treated groups are made using the method of Litchfield and Wilcoxon (1949)[3].

In control animals the CC$_{50}$ is usually 14–18 mA. Hence the first animal in the control group is subjected to a current of 16 mA. If a tonic seizure does not ensue, the current is increased for a subsequent mouse. If a tonic convulsion does occur, then the current is decreased, and so on until all the animals in the group have been tested.

Studies are carried out using a Hugo Sachs Electronik Constant Current Shock Generator with totally variable control of shock level from 0 to 300 mA and steps of 2 mA are usually used.

Results

Compounds of this invention dosed at 10 mg/kg by the oral route as a suspension in methyl cellulose and tested one hour post dosing showed an increase in seizure threshold.

Method for Rat Model

The threshold for maximal (tonic hindlimb extension) electroshock seizures in male rats (Sprague Dawley, 80–150 g, 6 weeks old) was determined by a Hugo Sachs Electronik stimulator which delivered a constant current (0.3 sec duration; from 1–300 mA in steps of 5–2 mA). The procedure is similar to that outlined above for mouse and full details are as published by Upton et al,.[4]

The percentage increase or decrease in $CC_{50}$ for each group compared to the control is calculated. Drugs are suspended in 1% methyl cellulose.

Results

At a dosage of 2 mg/ka p.o. at 2 h, the compounds of Examples 2, 3, 5, 7 and 8 gave significant increases of 390, 140, 210, 410 and 114% respectively.

REFERENCES

1. Loscher, W. and Schmidt, D. (1988). Epilepsy Res., 2, 145–181
2. Dixon, W. J. and Mood, A. M. (1948). J. Amer. Stat. Assn., 43, 109–126
3. Litchfield, J. T. and Wilcoxon, F.(1949). J. Pharmacol. exp. Ther., 96, 99–113
4. N. Upton, T. P. Blackburn, C. A. Campbell, D. Cooper, M. L. Evans, H. J. Herdon, P. D. King, A. M. Ray, T. O. Stean, W. N. Chan, J. M. Evans and M. Thompson. (1997). B. J. Pharmacol., 121, 1679–1686

What is claimed is:

1. A compound of formula (I):

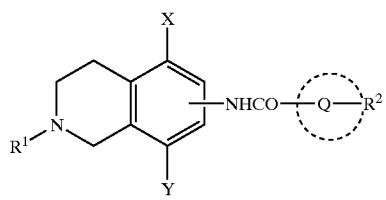

(I)

wherein:

Q is a monocyclic or bicyclic aryl or heteroaryl ring;

$R^1$ is hydrogen;

$R^2$ is hydrogen or up to three substituents selected from halogen, $NO_2$, CN, $N_3$, $CF_3O$—, $CF_3S$—, $CF_3SO_2$—, $CF_3CO$—, $C_{1-6}$alkyl, $C_{1-6}$alkenyl, $C_{1-6}$alkynyl, $C_{1-6}$perfluoroalkyl, $C_{3-6}$cycloalkyl, $C_{3-6}$cycloalkyl-$C_{1-4}$alkyl-, $C_{1-6}$alkylO—, $C_{1-6}$alkylCO—, $C_{3-6}$cycloalkylO—, $C_{3-6}$cycloalkylCO—, $C_{3-6}$cycloalkyl-$C_{1-4}$alkylO—, $C_{3-6}$cycloalkyl-$C_{1-4}$alkylCO—, phenyl, phenoxy, benzyloxy, benzoyl, phenyl-$C_{1-4}$alkyl-, $C_{1-6}$alkylS—, $C_{1-6}$alkylSO_2$—, $(C_{1-4}$alkyl$)_2$NSO_2$—, $(C_{1-4}$alkyl$)$NHSO_2$—, $(C_{1-4}$alkyl$)_2$NCO—, $(C_{1-4}$alkyl$)$NHCO—, or $CONH_2$, or —$NR^3R^4$ where $R^3$ is hydrogen or $C_{1-4}$ alkyl, and $R^4$ is hydrogen, $C_{1-4}$alkyl, formyl, —$CO_2C_{1-4}$alkyl, or —$COC_{1-4}$alkyl, or two $R^2$ groups together form a carbocyclic ring that is saturated or unsaturated and unsubstituted or substituted by —OH or =O;

X is halogen, $C_{1-6}$ alkoxy, $C_{1-6}$ alkyl, or $C_{1-6}$ perfluoroalkyl, and;

Y is hydrogen, halogen, $C_{1-6}$ alkoxy, $C_{1-6}$ alkyl, or $C_{1-6}$ perfluoroalkyl; but excluding the compounds N-(5-Iodo-1,2,3,4-tetrahydroisoquinolin-7-yl)-4-azidobenzamide and N-(5-iodo-1,2,3,4-tetrahydroisoquinolin-7-yl)-5-benzoyl-2-methoxybenzamide;

or a pharmaceutically acceptable salt or solvate thereof.

2. A compound of formula (I) according to claim 1 which is a compound of formula (IA):

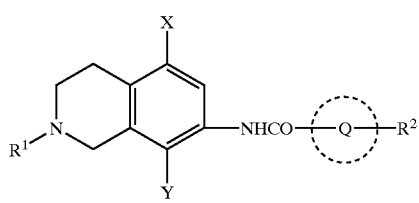

IC wherein $R^1$, $R^2$, X, and Y are as defined in claim 1.

3. A compound of formula (I) which is a compound of formula (IB):

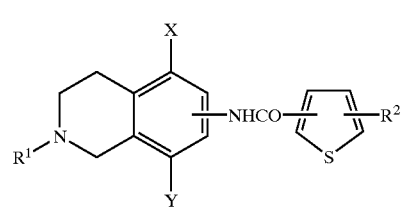

(IA)

wherein $R^1$, $R^2$, X, and Y are as defined in claim 1.

4. A compound of formula (I) according to claim 1 that is N-(5-Chloro-1,2,3,4-tetrahydroisoquinolin-7-yl)-3-chloro-4-ethoxy benzamide; or a pharmaceutically acceptable salt or solvate thereof.

wherein $R^1$, $R^2$, X, and Y are as hereinbefore defined.

5. A compound according to claim 1, in which $R^1$ is hydrogen;

$R^2$ is hydrogen or one or more of the following groups; methyl, ethyl, n-butyl, iso-propyl, t-butyl, phenyl, methoxy, ethoxy, iso-propoxy, n-butoxy, cyclopropylmethoxy, phenoxy, benzyloxy, amino, acetylamino, nitro, azido, cyano, bromo, chloro, fluoro, iodo, acetyl, pivaloyl, iso-butyroyl, benzoyl, iodobenzoyl, trifluoromethyl, perfluoroethyl, trifluoromethoxy, trifluoroacetyl, methanesulfonyl, n-propylsulfonyl, isopropylsulfonyl, dimethylsulfamoyl, or two $R^2$ groups form a benzene, cyclopentane or cyclopentanone ring;

X is chloro, bromo, iodo, fluoro $C_{1-6}$ perfluoroalkyl, and;

Y is hydrogen, halogen, $C_{1-6}$ alkoxy, $C_{1-6}$ alkyl, or , $C_{1-6}$ perfluoroalkyl.

6. A compound according to claim 1, in which $R^1$ is hydrogen;

$R^2$ is hydrogen or one or more of the following groups; methyl, ethyl, iso-propyl, n-butyl, t-butyl, phenyl, methoxy, ethoxy, iso-propoxy, phenoxy, acetoxy, nitro, cyano, bromo, chloro, fluoro, iodo, acetyl, pivaloyl, trifluoromethyl, pentafluoroethyl, azido, trifluoromethoxy;

X is iodo, chloro, bromo or trifluoromethyl, and;

Y is hydrogen, chloro, bromo, iodo or trifluoromethyl.

7. A compound of formula (I) according to claim 1 which is:

N-(5-Chloro-1,2,3,4-tetrahydroisoquinolin-7-yl)-5-chlorothiophene-2-carboxamide
N-(5-Chloro-1,2,3,4-tetrahydroisoquinolin-7-yl)-3-chloro-4-ethoxy benzamide
N-(5-Chloro-1,2,3,4-tetrahydroisoquinolin-7-yl)-3-cyano-4-iso-propyl benzamide
N-(5-Chloro-1,2,3,4-tetrahydroisoquinolin-7-yl)-4-methoxy-3-trifluoromethyl benzamide
N-(5-Chloro-1,2,3,4-tetrahydroisoquinolin-7-yl)-3-cyano-4-methoxybenzamide
N-(5-Chloro-1,2,3,4-tetrahydroisoquinolin-7-yl)-3-chloro-4-methoxybenzamide
N-(5-Chloro-1,2,3,4-tetrahydroisoquinolin-7-yl)-3-bromo-4-ethoxybenzamide
N-(5-Chloro-1,2,3,4-tetrahydroisoquinolin-7-yl)-3-acetyl-4-iso-propoxybenzamide
N-(5-Chloro-1,2,3,4-tetrahydroisoquinolin-7-yl)-3-acetyl-4-ethylbenzamide
N-(5-Chloro-1,2,3,4-tetrahydroisoquinolin-7-yl)-3-bromo-4-ethylbenzamide
N-(5-Chloro-1,2,3,4-tetrahydroisoquinolin-7-yl)-3-chloro-4-iso-propoxybenzamide
N-(5-Chloro-1,2,3,4-tetrahydroisoquinolin-7-yl)-4-ethoxy-3-trifluoromethyl benzamide
N-(5-Chloro-1,2,3,4-tetrahydroisoquinolin-7-yl)-3-cyano-4-ethoxy benzamide
N-(5-Chloro-1,2,3,4-tetrahydroisoquinolin-7-yl)-3-acetyl-4-ethoxy benzamide
N-(5-Chloro-1,2,3,4-tetrahydroisoquinolin-7-yl)-4-ethyl-3-trifluoromethyl benzamide
N-(5,8-Dichloro-1,2,3,4-tetrahydroisoquinolin-7-yl)-4-methoxy-3-trifluoromethylbenzamide
N-(5-Chloro-1,2,3,4-tetrahydroisoquinolin-7-yl)-3-bromo-4-methoxybenzamide
N-(5-Chloro-1,2,3,4-tetrahydroisoquinolin-7-yl)-3-fluoro-4-methoxybenzamide
N-(5-Chloro-1,2,3,4-tetrahydroisoquinolin-7-yl)-3-bromo-4-iso-propoxybenzamide
N-(5-Chloro-1,2,3,4-tetrahydroisoquinolin-7-yl)-4-methoxy-3-pentafluoroethyl benzamide
N-(5-Chloro-1,2,3,4-tetrahydroisoquinolin-7-yl)-4-iso-propoxy-3-trifluoromethyl benzamide
N-(5-Bromo-1,2,3,4-tetrahydroisoquinolin-7-yl)-3-bromo-4-methoxybenzamide
N-(5-Bromo-1,2,3,4-tetrahydroisoquinolin-7-yl)-4-methoxy-3-trifluoromethyl benzamide
N-(5-Bromo-1,2,3,4-tetrahydroisoquinolin-7-yl)-4-ethoxy-3-trifluoromethyl benzamide
N-(5-Bromo-1,2,3,4-tetrahydroisoquinolin-7-yl)-3-cyano-4-ethoxybenzamide
N-(5-Bromo-1,2,3,4-tetrahydroisoquinolin-7-yl)-3-acetyl-4-ethoxybenzamide
N-(5-Bromo-1,2,3,4-tetrahydroisoquinolin-7-yl)-3-acetyl-4-iso-propoxybenzamide
N-(5-Bromo-1,2,3,4-tetrahydroisoquinolin-7-yl)-3-chloro-4-ethoxybenzamide
N-(5-Bromo-1,2,3,4-tetrahydroisoquinolin-7-yl)-3-bromo-4-ethoxybenzamide
N-(5-Bromo-1,2,3,4-tetrahydroisoquinolin-7-yl)-3-cyano-4-iso-propylbenzamide
N-(5-Trifluoromethyl-1,2,3,4-tetrahydroisoquinolin-7-yl)-3-chloro-4-ethoxybenzamide
N-(5-Trifluoromethyl-1,2,3,4-tetrahydroisoquinolin-7-yl)-4-methoxy-3-trifluoromethylbenzamide
N-(5-Trifluoromethyl-1,2,3,4-tetrahydroisoquinolin-7-yl)-3-fluoro-4-methoxy-benzamide
N-(5,8-Dichloro-1,2,3,4-tetrahydroisoquinolin-7-yl)-3-chloro-4-ethoxybenzamide
N-(5,8-Dichloro-1,2,3,4-tetrahydroisoquinolin-7-yl)-3-bromo-4-ethoxybenzamide
N-(5,8-Dichloro-1,2,3,4-tetrahydroisoquinolin-7-yl)-3-cyano-4-ethoxybenzamide
N-(5,8-Dichloro-1,2,3,4-tetrahydroisoquinolin-7-yl)-3-acetyl-4-ethoxybenzamide
N-(5,8-Dichloro-1,2,3,4-tetrahydroisoquinolin-7-yl)-3-fluoro-4-methoxybenzamide
N-(5,8-Dichloro-1,2,3,4-tetrahydroisoquinolin-7-yl)-3-bromo-4-methoxybenzamide
N-(5,8-Dichloro-1,2,3,4-tetrahydroisoquinolin-7-yl)-3-acetyl-4-iso-propoxybenzamide, or
N-(5-Chloro-1,2,3,4-tetrahydroisoquinolin-7-yl)-3-cyano-4-iso-propoxybenzamide; or a pharmaceutically acceptable salt or solvate thereof.

8. A process for the preparation of a compound according to claim 1, which comprises reacting a compound of formula (II):

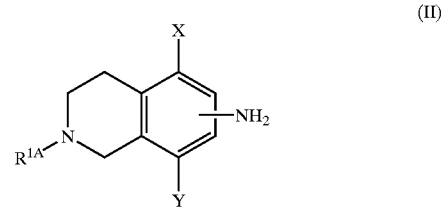

wherein $R^{1A}$ is $R^1$ or a group convertible to $R^1$, and $R^1$, X, and Y are as defined in claim 1, with a compound of formula (III):

wherein Q is as defined in claim 1;

Y is a leaving group, and;

$R^{2A}$ represents hydrogen or up to three substituents as defined in claim 1 for $R^2$ wherein the $R^{2A}$ groups may independently be $R^2$ groups or groups convertible to $R^2$; and where required converting an $R^{1A}$ or $R^{2A}$ group to a $R^1$ or $R^2$ group respectively;

converting one $R^1$ or $R^2$ group to another $R^1$ or $R^2$ group; converting a salt product to the free base or a pharmaceutically acceptable salt, or converting a free base product to a pharmaceutically acceptable salt.

9. A pharmaceutical composition comprising a compound according to claim 1, and a pharmaceutically acceptable carrier.

10. A method of treatment and/or prophylaxis of anxiety, mania, depression, panic disorders and/or aggression, disorders associated with a subarachnoid hemorrhage or neural shock, the effects associated with withdrawal from cocaine, nicotine, alcohol, benzodiazepines and other substances of abuse, epilepsy, post-traumatic epilepsy and other disorders treatable and/or preventable with anti-convulsive agents, Parkinson's disease, psychosis, migraine, cerebral ischaemia, Alzheimer's disease, Huntingdon's chorea, and other degenerative diseases, schizophrenia, obsessive compulsive disorders (OCD), neurological deficits associated with AIDS, circadian rhythm disorders, insomnia, narcolepsy and other sleep disorders, Giles de la Tourette's syndrome and other tics, traumatic brain injury, tinnitus, neuralgia, trigeminal neuralgia, neuropathic pain, dental pain, cancer pain, inappropriate neuronal activity resulting in neurodysthesias, ataxias, muscular rigidity, temporomandibular joint dysfunction, or amyotrophic lateral sclerosis (ALS) comprising administering to the sufferer in need thereof an effective or prophylactic amount of a compound according to claim 1.

11. The method of claim 10 wherein the disease state is selected from epilepsy, neuropathic pain and the prophylaxis of migrane.

12. The method of claim 11 wherein the compound is N-(5-Chloro-1,2,3,4-tetrahydroisoquinolin-7-yl)- 3-chloro-4-ethoxy benzamide; or a pharmaceutically acceptable salt or solvent thereof.

13. A composition according to claim 9 wherein the compound is N-(5-Chloro-1,2,3,4-tetrahydroisoquinolin-7-yl)-3-chloro-4-ethoxy benzamide; or a pharmaceutically acceptable salt or solvate thereof.

14. A compound of formula (I) according to claim 1 which is a compound of formula 1C:

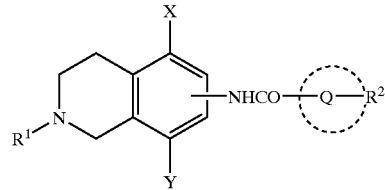

1C wherein $R^1$, $R^2$, X, and Y are as defined in claim 1.

* * * * *